United States Patent [19]

Lazzarini et al.

[11] Patent Number: 4,624,956
[45] Date of Patent: Nov. 25, 1986

[54] ULCER AND GASTRIC SECRETION INHIBITING 4,5,6,7-TETRAHYDROTHIAZOLE[5,4-C]PYRIDINE DERIVATIVES

[75] Inventors: Anna M. Lazzarini, Seregno; Ugo Scarponi, Arese; Roberto de Castiglione, Milan; Roberto Ceserani, Milan; Renato Castello, Milan; Fabrizio Vaghi, Villaguardia; Daniela Toti, Bettola, all of Italy

[73] Assignee: Farmitalia Carlo Erba, Milan, Italy

[21] Appl. No.: 680,566

[22] Filed: Dec. 11, 1984

[30] Foreign Application Priority Data

Dec. 16, 1983 [GB] United Kingdom ............... 8333514

[51] Int. Cl.$^4$ .................. A61K 31/445; C07D 513/04
[52] U.S. Cl. .................................... 514/301; 544/127; 544/362; 546/114
[58] Field of Search ............... 546/114; 544/106, 362; 424/256; 514/301

[56] References Cited

FOREIGN PATENT DOCUMENTS 1140387 1/1969 United Kingdom ............... 546/114

Primary Examiner—Richard A. Schwartz
Assistant Examiner—Kurt G. Briscoe
Attorney, Agent, or Firm—Oblon, Fisher, Spivak, McClelland, & Maier

[57] ABSTRACT

A compound of formula I:

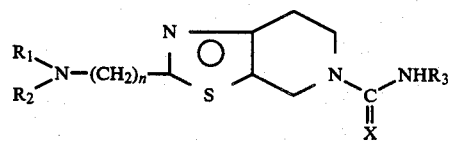

wherein either (i) each of $R_1$ and $R_2$ independently represents a hydrogen atom or an organic group, or (ii) $R_1$ and $R_2$ linked together form a heterocyclic ring or (iii) $R_2$ is hydrogen and $R_1$ is

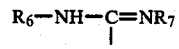

wherein each of $R_6$ and $R_7$ independently represents hydrogen or an organic group, n is 0-3, X is O, S, NH, $NR_8$, $CHNO_2$ or $CHSO_2R_4$, wherein $R_8$ and $R_4$ are organic groups and $R_3$ represents an organic group. The compound of formula I is effective as an anti-ulcer agent and is highly effective as a histamine $H_2$-receptor antagonist.

10 Claims, No Drawings

ULCER AND GASTRIC SECRETION INHIBITING 4,5,6,7-TETRAHYDROTHIAZOLE[5,4-C]PYRIDINE DERIVATIVES

FIELD OF THE INVENTION

The present invention relates to 4,5,6,7-tetrahydrothiazole[5,4-c]pyridine derivatives, to processes for their preparation and to pharmaceutical compositions containing the same.

The present invention is directed to 4,5,6,7-tetrahydrothiazole[5,4-c]pyridine derivatives of formula I:

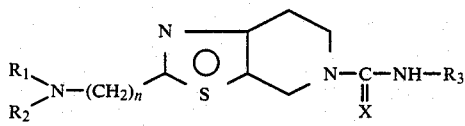

wherein n is zero or an integer of from 1 to 3; either (i) each of $R_1$ and $R_2$ independently represents a hydrogen atom, a saturated or unsaturated, linear or branched alkyl group having from 1 to 6 carbon atoms, a cycloalkyl group having from 3 to 7 carbon atoms, a phenyl group, a mono- or di-substituted phenyl group (the substituent(s) being selected from alkyl, alkoxy, alkylthio or alkylsulfonyl groups having from 1 to 4 carbon atoms, amino, alkylamino, acylamino, aminosulfonyl, hydroxy, nitro, carboxy, carboxamido or methylenedioxy groups or fluorine, chlorine or bromine atoms) or an acyl group of the formula $R_4CO$ wherein $R_4$ represents a lower alkyl group, a phenyl group or a mono- or di-substituted phenyl group (the substituents being as above defined) or (ii) $R_1$ and $R_2$ together with the nitrogen atom to which they are attached form a phthalamido group or a 5- or 6-membered heterocyclic ring which may contain other heteroatoms selected from oxygen and nitrogen, with any hydrogen bearing nitrogen ring atom optionally being alkylated, or (iii) $R_2$ represents a hydrogen atom and $R_1$ represents an amidino group of the formula

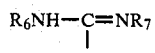

wherein each of $R_6$ and $R_7$ independently represents a hydrogen atom, a linear or branched alkyl group having from 1 to 4 carbon atoms, a cycloalkyl group having from 3 to 7 carbon atoms or a functionalized chain such as those of the formula $(CH_3)_2N-(CH_2)_m$ and

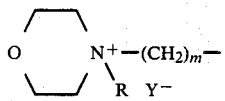

wherein m is an integer of from 1 to 3, R represents a lower alkyl group and $Y^-$ represents a bromide, chloride or p-toluenesulfonate anion;

X represents an oxygen or sulfur atom, an imino group or a group of the formula $NR_8$, $CHNO_2$ or $CHSO_2R_4$, wherein $R_8$ represents a lower alkyl, cyano, nitro, amino, acylamino, carboxamido or lower alkoxycarbonyl group or a group of the formula $COR_4$ or $SO_2R_4$, wherein $R_4$ is as above defined; and $R_3$ represents a phenylethyl, a saturated or unsaturated, linear or branched alkyl group having from 1 to 6 carbon atoms, a cycloalkyl group having from 3 to 7 carbon atoms, a phenyl group, a mono- or di-substituted phenyl group (the substituents being as above defined), a benzyl group, a mono- or di-substituted benzyl group (the substituents being as above defined for a phenyl group), or a group of the formula $COR_4$ or $SO_2R_4$ wherein $R_4$ is as above defined; and further provides pharmaceutically acceptable acid addition salts thereof.

In the formula above, when $R_1$, $R_2$, $R_3$, $R_4$, $R_6$, $R_7$, $R_8$, and R are each an alkyl group, they are preferably methyl, ethyl, n-propyl, i-propyl, sec.butyl, i-butyl, t-butyl or n-butyl. When groups $R_1$, $R_2$, $R_3$, $R_6$ and $R_7$ are a cycloalkyl, they are preferably cyclopropyl, cyclopentyl, cyclohexyl or cycloheptyl. When groups $R_1$ and $R_2$ together with the nitrogen atom to which they are attached form a heterocyclic ring, they preferably form a piperidino, piperazino, morpholino or pyrrolidino ring. When $R_8$ represents an acylamino group, it is preferably benzoylamino or acetylamino. When $R_8$ represents an alkoxycarbonyl group, it is preferably methoxycarbonyl or ethoxycarbonyl.

The acid addition salts of the compound of formula I may be derived from a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicyclic, gluconic, ascorbic and related acids.

In formula (I) above, n is preferably 0 or 1, more preferably 0.

With regard to substituents $R_1$ and $R_2$, preferably each of the same independently represents a hydrogen atom or an alkyl group having from 1 to 6 carbon atoms, more preferably a methyl group, or $R_2$ represents a hydrogen atom and $R_1$ represents an amidino group of the formula

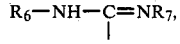

wherein each of $R_6$ and $R_7$ independently represents a hydrogen atom or a cycloalkyl group having from 3 to 7 carbon atoms. Most preferably $R_6$ and $R_7$ represent hydrogen atoms.

In formula (I) above, $R_3$ preferably represents a methyl, ethyl, i-propyl, n-butyl, phenyl, benzoyl, benzyl, cyclopropyl, cyclopentyl, cyclohexyl or p-toluenesulfonyl group, more preferably an i-propyl group.

Preferably X represents an oxygen or sulfur atom, an imino, cyanoimino, o-toluenesulfonyl-imino or benzoylimino group, most preferably an oxygen atom.

Specific examples of preferred compounds of the invention are:

2-amino-5-(methyl-thiocarbamoyl)-4,5,6,7-tetrahydrothiazolo[5,4-c]pyridine, 2-amino-5-(isopropyl-thiocarbamoyl)-4,5,6,7-tetrahydrothiazolo[5,4-c]pyridine, 2-amino-5-(phenyl-thiocarbamoyl)-4,5,6,7-tetrahydrothiazolo[5,4-c]pyridine, 2-amino-5-(benzoyl-thiocarbamoyl)-4,5,6,7-tetrahydrothiazolo[5,4-c]pyridine, 2-amino-5-(methyl-carbamoyl)-4,5,6,7-tetrahydrothiazolo[5,4-c]pyridine, 2-amino-5-(isopropyl-carbamoyl)-4,5,6,7-tetrahydrothiazolo[5,4-c]pyridine,
2-amino-5-(phenyl-carbamoyl)-4,5,6,7-tetrahydrothiazolo[5,4-c]pyridine,
2-amino-5-(N-benzylcarbamoyl)-4,5,6,7-tetrahydrothiazolo[5,4-c]pyridine,
2-amino-5-(N-cyano-N'-methyl-amidino)-4,5,6,7-tetrahydrothiazolo[5,4-c]pyridine,
2-amino-5-(N-cyano-N'-isopropyl-amidino)-4,5,6,7-tetrahydrothiazolo[5,4-c]pyridine,
2-amino-5-(N-cyano-N'-benzyl-amidino)-4,5,6,7-tetrahydrothiazolo[5,4-c]pyridine,
2-amino-5-(N'-benzoyl-amidino)-4,5,6,7-tetrahydrothiazolo[5,4-c]pyridine,
2-amino-5-(N'-methyl-N-tosyl-amidino)-4,5,6,7-tetrahydrothiazolo[5,4-c]pyridine,
2-amino-5-(N'-methyl-N-benzoyl-amidino)-4,5,6,7-tetrahydrothiazolo[5,4-c]pyridine,
2-guanidino-5-(isopropyl-thiocarbamoyl)-4,5,6,7-tetrahydrothiazolo[5,4-c]pyridine,
2-guanidino-5-(isopropyl-carbamoyl)-4,5,6,7-tetrahydrothiazolo[5,4-c]pyridine,
2-guanidino-5-(N'-methyl-N-cyano-amidino)-4,5,6,7-tetrahydrothiazolo[5,4-c]pyridine,
2-guanidino-5-(N'-benzoyl-amidino)-4,5,6,7-tetrahydrothiazolo[5,4-c]pyridine,
2-guanidino-5-(N'-methyl-N-tosyl-amidino)-4,5,6,7-tetrahydrothiazolo[5,4-c]pyridine,
2-guanidino-5-(N'-methyl-N-benzoyl-amidino)-4,5,6,7-tetrahydrothiazolo[5,4-c]pyridine,
2-(N,N'-dicyclohexylguanidino)-isopropylcarbamoyl-4,5,6,7-tetrahydrothiazolo[5,4-c]pyridine,
2-guanidino-5-(cyclopropyl-carbamoyl)-4,5,6,7-tetrahydrothiazolo[5,4-c]pyridine,
2-guanidino-5-(cyclopentyl-carbamoyl)-4,5,6,7-tetrahydrothiazolo[5,4-c]pyridine,
2-guanidino-5-(methyl-carbamoyl)-4,5,6,7-tetrahydrothiazolo[5,4-c]pyridine,
2-guanidino-5-(cyclohexyl-carbamoyl)-4,5,6,7-tetrahydrothiazolo[5,4-c]pyridine,
2-guanidino-5-(tosyl-carbamoyl)-4,5,6,7-tetrahydrothiazolo[5,4-c]pyridine,
2-guanidino-5-(ethyl-carbamoyl)-4,5,6,7-tetrahydrothiazolo[5,4-c]pyridine,
2-guanidino-5-(n-propyl-carbamoyl)-4,5,6,7-tetrahydrothiazolo[5,4-c]pyridine,
2-guanidino-5-(n-butyl-carbamoyl)-4,5,6,7-tetrahydrothiazolo[5,4-c]pyridine,
2-(N,N-dimethylaminomethyl)-5-(N-isopropylthiocarbamoyl)-4,5,6,7-tetrahydrothiazolo[5,4-c]pyridine,
2-(N,N-dimethylaminomethyl)-5-(N-isopropylcarbamoyl)-4,5,6,7-tetrahydrothiazolo[5,4-c]pyridine,
2-(N,N-dimethylaminomethyl)-5-(N-cyano-N'-methyl-guanyl)-4,5,6,7-tetrahydrothiazolo[5,4-c]pyridine,
2-amino-5-(2'-phenylethyl-carbamoyl)-4,5,6,7-tetrahydrothiazolo[5,4-c]pyridine,
2-guanidino-5-(2'-phenylethyl-carbamoyl)-4,5,6,7-tetrahydrothiazolo[5,4-c]pyridine,
2-guanidino-5-(phenyl-carbamoyl)-4,5,6,7-tetrahydrothiazolo[5,4-c]pyridine,
2-guanidino-5-(phenyl-thiocarbamoyl)-4,5,6,7-tetrahydrothiazolo[5,4-c]pyridine,
2-guanidino-5-(benzyl-carbamoyl)-4,5,6,7-tetrahydrothiazolo[5,4-c]pyridine,
2-amino-5-(4'-chlorophenyl-carbamoyl)-4,5,6,7-tetrahydrothiazolo[5,4-c]pyridine,
2-guanidino-5-(4'-chlorophenyl-carbamoyl)-4,5,6,7-tetrahydrothiazolo[5,4-c]pyridine,
2-amino-5-(cyclobutyl-carbamoyl)-4,5,6,7-tetrahydrothiazolo[5,4-c]pyridine,
2-guanidino-5-(cyclobutyl-carbamoyl)-4,5,6,7-tetrahydrothiazolo[5,4-c]pyridine.

The present invention further provides a process for the preparation of 4,5,6,7-tetrahydrothiazolo[5,4-c]pyridine derivatives of formula I, wherein X represents an oxygen or sulfur atom or an imino group and $R_1$, $R_2$, $R_3$ and n are each as above defined, the process comprising condensing a 4,5,6,7-tetrahydrothiazolo[5,4-c]pyridine derivative of formula II

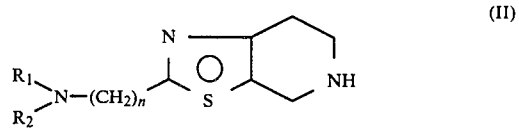

(II)

wherein $R_1$, $R_2$ and n are each as above defind with an isocyanate, isothiocyanate or N-substituted cyanamide of formula III

(III)

wherein $R_3$ is as defined above and X' represents an oxygen or sulfur atom or an imino group.

The present invention also provides a process for the preparation of 4,5,6,7-tetrahydrothiazolo[5,4-c]pyridine derivatives of formula I, wherein X represents a group of the formula $NR_8$, $CHNO_2$ or $CHSO_2R_4$ as defined above, and $R_3$ is as defined above and further it can also be a group of the formula $COR_4$ or $SO_2R_4$, and wherein $R_1$, $R_2$ and n are as defined above, the process comprising condensing a 4,5,6,7-tetrahydrothiazolo[5,4-c]pyridine derivative of formula II as shown above with a compound of formula IV

IV wherein X'' represents a group of the formula $NR_8$, $CHNO_2$ or $CHSO_2R_4$ as defined above, and treating the resultant compound of formula V

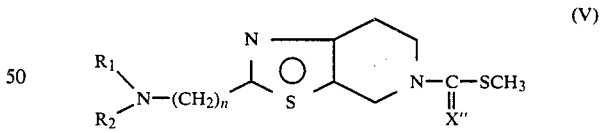

(V)

wherein $R_1$, $R_2$, X'' and n are as defined above with an amine of the formula $R_3NH_2$, wherein $R_3$ is as described above and further can also be a group of the formula $COR_4$ or $SO_2R_4$.

The compounds of formula I, wherein $R_2$ represents a hydrogen atom, $R_1$ represents a group of the formula $$R_6NH-C=NR_7,$$

wherein $R_6$ and $R_7$ are as defined above except hydrogen, and $R_3$, X and n are as defined above may be prepared from the compounds of formula I, wherein $R_1$ and $R_2$ both represent hydrogen atoms and $R_3$, X and n are as defined above by reacting the latter with a carbodiimide of formula VI

$$R_6-N=C=N-R_7 \quad (VI)$$

wherein $R_6$ and $R_7$ are each as previously defined except hydrogen. This process is also within the scope of the invention.

The starting compounds of formula II may be prepared by condensing a hydrohalic acid salt of 3-bromo-4-piperidone with a reagent of formula VII

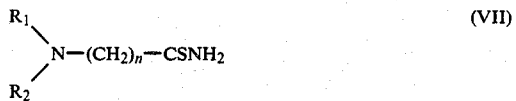

$$\begin{array}{c} R_1 \\ \diagdown \\ N-(CH_2)_n-CSNH_2 \\ \diagup \\ R_2 \end{array} \quad (VII)$$

wherein $R_1$, $R_2$ and n are as defined above by the general procedure for the preparation of thiazole rings well known to those skilled in the art.

The above described condensation reactions occur preferably in a solvent such as methanol, ethanol, acetonitrile, dioxane or dimethylformamide at a temperature ranging from 0° C. to 165° C. The products can be isolated from the reaction mixtures either as free bases by crystallization or by chromatography, or as salts of pharmaceutically acceptable acids. The 4,5,6,7-tetrahydrothiazolo[5,4-c]pyridine derivatives of the invention have proved to be well tolerated by experimental animals after oral or parenteral administration and to be active in the gastroenterical system. In particular, they inhibit the number of experimental ulcers and gastric secretion in experimental animals, and are highly effective histamine $H_2$-receptor antagonists. They should thus prove useful in therapy, for example, in the prevention and treatment of peptic ulcers such as duodenal, gastric and oesophageal ulcers.

Thus, the present invention provides a pharmaceutical composition comprising 4,5,6,7-tetrahydrothiazolo[5,4-c]pyridine derivative or a pharmaceutically acceptable salt thereof in admixture with a pharmaceutically acceptable diluent or carrier.

The activity of embodiments of the present compound was assessed in rats in anti-ulcer and anti-secretory tests.

The anti-ulcerogenic activity of the present compound is shown, for example, by the fact that embodiments of the present compound are active in the test of inhibition of acetyl salicyclic acid (ASA) induced gastric ulcers in rats as described by M. Hemmati et al in Pharmacology, 9, 374, 1973. Male Sprague Dawley rats [Crl: CD (SD) BR] (Charles River Italy) weighing 190±10 g, which had fasted for 15 hours, but given free access to water, were administered ASA (100 mg/kg per os in 0.2 ml/100 g b.w.) 60 minutes after the oral treatment with the tested compounds. Gastric ulcerations were evaluated 4 hours after ASA treatment. The inhibition of gastric ulcerations, evaluated as percentage inhibition of ulcer index (sum of ulcer length in millimeters), was expressed as $ED_{50}$ (dose which reduces gastric ulcerations by 50% in comparison with control rats). The results are reported in column 1 of Table 1.

The anti-ulcerogenic activity of the compound of the present invention is shown also by the fact that embodiments of the same are active in the test of inhibition of stress ulcers in rats (restraint in water at 23° C. for 4 hours), according to the method of M. Usardi et al. (Prostaglandins, 8, 43, 1974). The tested compounds were administered per os one hour before the stress. Six Charles River male rats (140±10 g body weight), which had fasted for 16 hours, were used for each experimental group. At the end of the stress, the rats were killed and the gastric ulcers evaluated by counting them.

The inhibition of gastric ulcerations, evaluated as percentage inhibition of ulcer index (number of ulcers), was expressed as $ED_{50}$. The results are reported in column 2 of Table 1.

The inhibition of duodenal ulcers, induced in rats by cysteamine, was evaluated for the tested compounds as percentage inhibition of ulcer index [sum of the lesioned areas per rat (mm$^2$)] according to the method of Fujii Y. et al, Jap. J. Pharm. 25, 663, 1975, and expressed as $ED_{50}$. The data are reported in column 3 of Table 1.

The gastric anti-secretory activity of the compound of the present invention was evaluated in rats by the pylorus ligature technique (H. Shay et al, Gastroenterology 5, 43 1945). Six Sprague-Dawley male rats (110-130 g body weight) for each group were used. Twenty-four hours before the test, the rats were deprived of food while water was maintained. On the day of operation, the pylorus was ligated under light ether anaesthesia. Four hours after the ligature the rats were sacrificed, the stomach secretion collected, centrifuged at 3500 r.p.m. for 10 minutes and the volume, less sediment, was determined. The amount of free hydrochloric acid in the gastric juice was determined by titration against 0.1N sodium hydroxide to an end point of pH 7. All the compounds were injected intraduodenally at the time of ligature. The results, expressed as $ED_{50}$ mg/kg (the dose which reduced the output of hydrochloride acid by 50% in comparison with control rats) are reported in column 4 of Table 1.

The compound of the present invention was assayed for histamine $H_2$-receptor antagonist activity in vitro on the guinea pig right atrium. Male guinea pigs were killed by a blow on the head and the heart was quickly excised and placed in oxygenated Ringer Lock solution of the following composition (g/l): NaCl 9, KCl 0.42, $CaCl_2$ 0.24, $NaHCO_3$ 0.5, Glucose 1. Atria were dissected away from the rest of the heart, freed from connective tissue, suspended in a 20 ml organ bath containing Ringer Locke solution thermoregulated at 37° C., and carboxygenated with 95% $O_2$ and 5% $CO_2$. Atria spontaneously beating were allowed to adjust to the bath conditions for at least 30 minutes prior to the experiment. Histamine was added to the bath in cumulative fashion starting from $3\times10^{-7}$M to $1\times10^{-4}$M. The histamine-induced increase in atrial rate was allowed to plateau before the next successive concentration was added. After washing and waiting for the recovery of atria rate, a compound was added 5 minutes before repeating the cumulative dose response curve with histamine. A compound is considered an $H_2$-receptor antagonist if it is able to shift the dose response curve of histamine to the right at a concentration $\leq 1\times10^{-5}$M. The results are reported in column 5 of Table 1.

Considering that some anti-ulcer agents display, as does atropine, a remarkable but undesired anticholinergic activity, the compound of the present invention was also assessed for its antagonism against the syndrome induced by intraperitoneally (i.p.) administered oxotremorine in mice, according to the method described by G. P. Leszkovsky and L. Tardos (Europ. J. Pharmac. 1971, 15, 310). Given test compound embodiments were administered to groups of 5 male mice, 20-25 g body weight, at the screening dose of 100 mg/kg per os. The degree of peripheral cholinergic activation induced by oxotremorine was measured b salivation and lachrymation, and the degree of central cholinergic activation by the severity of tremors and hypothermia. Atropine sulfate suppressed both peripheral and central effects induced by oxotremorine. The results are reported in column 6 of Table 1. The approximate acute toxicity ($LD_{50}$) of the compounds of the invention was determined in the mouse and in the rat by single oral administration of increasing doses and measured on the seventh day after treatment. The results are reported in column 7 of Table 1. Ranitidine, the well known anti-ulcer agent, was used as comparison compound.

the pure title compound (m.p. 188°–190° C. with decomposition) were obtained.

EXAMPLE 2

2-Amino-5-(isopropyl-thiocarbamoyl)-4,5,6,7-tetrahydrothiazolo[5,4-c]pyridine (n=0, $R_1=R_2=H$, $R_3=CH(H_3)_2$, X=S)-FCE 22828

Operating as in Example 1, but employing isopropyl thiocyanate instead of methyl isothiocyanate, the title compound (m.p. 179°–180° C. with decomposition) was obtained in 75% yield.

EXAMPLE 3

2-Amino-5-(phenyl-thiocarbamoyl)-4,5,6,7-tetrahydrothiazolo[5,4-c]pyridine (n=0, $R_1=R_2=H$, $R_3=C_6H_5$,

TABLE 1

| Compound Prepared in Example | Laboratory Code (FCE) | Biological Activities | | | | | | |
|---|---|---|---|---|---|---|---|---|
| | | Column 1 ASA | Column 2 Stress | Column 3 Cysteamine | Column 4 Antisecretory activ. | Column 5 Anti-$H_2$ activ. | Column 6 Anticholinergic activ. | Column 7 $LD_{50}$ Mouse | Rat |
| 2 | 22828 | ≃5 | 2.7 | — | 1 | — | Inactive | 400–800 | — |
| 5 | 22889 | 1.2 | >25 | — | >5 | — | Inactive | 200–400 | — |
| 15 | 22940 | 0.5 | <50 | — | <5 | Active | Inactive | 400–800 | — |
| 16 | 23067 | 0.017 | 2.9 | 0.4 | 0.33 | More active than Ranitid. | Inactive | 200–400 | >800 |
| 22 | 23712 | 0.08 | 20.2 | 0.3 | 1.7 | More active than Ranitid. | Inactive | >800 | >800 |
| Ranitidine | | 0.5 | 6.2 | 10.7 | 7 | | Inactive | >800 | >800 |

(1) Inhibition of gastric ulcers induced in rats by ASA (expressed as $ED_{50}$, mg/Kg p.o.).
(2) Inhibition of gastric ulcers induced in rats by stress (expressed as $ED_{50}$, mg/Kg p.o.).
(3) Inhibition of duodenal ulcers induced in rats by cysteamine (expressed as $ED_{50}$ mg/kg p.o.).
(4) Inhibition of basal gastric secretion output HCl (expressed as $ED_{50}$, mg, Kg i.d.) in rats.
(5) In vitro histamine $H_2$-receptor antagonist activity in guinea pig atria (screening dose of $1 \times 10^{-5}M$).
(6) Antagonism against oxotremorine syndrome in the mouse (screening dose of 100 mg/Kg p.o.).
(7) mg/Kg in the mouse and in the rat.

In the therapeutic field, the compound embodiments of the present invention may be administered by the oral or parenteral route. The therapeutic compositions normally employed should include one or more compounds of the present invention with a conventional quantity of a solid or a liquid vehicle. The compositions may be prepared as tablets, powders, pills or other forms pharmaceutically suitable for oral or parenteral administration. Liquid diluents duly sterilized are employed for the parenteral administration. Conventional excipients may be employed, among which the most common are starch, lactose, talc, magnesium stearate, and the like. The preferred oral dosage range in humans should be about 50 to 400 mg daily.

Having generally described the invention, a further understanding can be obtained by reference to certain specific examples which are provided herein for purposes of illustration only and are not intended to be limiting unless otherwise specified.

EXAMPLE 1

2-Amino-5-(methyl-thiocarbamoyl)-4,5,6,7-tetrahydrothiazolo[5,4-c]pyridine (n=0, $R_1=R_2=H$, $R_3=CH_3$, X=3)-FCE 2282

1.55 G (10 mmol) of 2-amino-4,5,6,7-tetrahydrothiazolo[5,4-c]pyridine was dissolved in 25 ml of dimethylformamide and the solution was cooled in an ice-water bath. 0.88 g (12 mmol) of methyl isothiocyanate was then added. After 7½ hours the solvent was removed by evaporation and the residue (about 2.2 g) was crystallized from acetonitrile. 1.25 g (55% yield) of

X=S)-FCE 22934

Operating as in Example 1, but employing phenyl isocyanate instead of methyl isothiocyanate, the title compound (m.p. 155°–157° C. with decomposition) was obtained in 40% yield.

EXAMPLE 4

2-Amino-5-(benzoyl-thiocarbamoyl)-4,5,6,7-tetrahydrothiazolo[5,4-c]pyridine (n=0, $R_1=R_2=H$, $R_3=COR_4$, X=S, $R_4=C_6H_5$)-FCE 2306

Operating as in Example 1, but employing benzoyl isothiocyanate instead of methyl isothiocyanate, the title compound (m.p. 158°–160° C.) was obtained in 43% yield.

EXAMPLE 5

2-Amino-5-(methyl-carbamoyl)-4,5,6,7-tetrahydrothiazolo[5,4-c]pyridine (n=0, $R_1=H$, $R_3=CH_3$, X=0) FCE-22889

Operating as in Example 1, but employing methyl isocyanate instead of methyl isothiocyanate, the title compound (m.p. 202° C. with decomposition) was obtained in 54% yield.

EXAMPLE 6

2-Amino-5-(isopropyl-carbamoyl)-4,5,6,7-tetrahydrothiazolo[5,4-c]pyridine (n=0, $R_1=R_2=H$, $R_3=CH(CH_3)_2$, X=0)-FCE 22829

Operating as in Example 1, but employing isopropyl isocyanate instead of methyl isothiocyanate, the title compound (m.p. 190°–192° C. with decomposition) was obtained in 54% yield.

EXAMPLE 7

2-Amino-5-(phenylcarbamoyl)-4,5,6,7-tetrahydrothiazolo[5,4-c]pyridine (n=0, $R_1=R_2=H$, $R_3=C_6H_5$, X=O)-FCE 22935

Operating as in Example 1, but employing phenyl isocyanate instead of methyl isothiocyanate, the title compound (m.p. 204°–206° C.) was obtained in 53% yield.

EXAMPLE 8

2-Amino-5-(N-benzylcarbamoyl)-4,5,6,7-tetrahydrothiazolo[5,4-c]pyridine (n=0, $R_1=R_2=H$, $R_3=CH_2C_6H_5$, X=O)-FCE 22951

Operating as in Example 1, but employing benzyl isocyanate instead of methyl isothiocyanate, the title compound (m.p. 197°–200° C.) was obtained in 47% yield.

EXAMPLE 9

2-Amino-5-(N-cyano-N'-methyl-amidino)-4,5,6,7-tetrahydrothiazolo[5,4-c]pyridine (n=0, $R_1=R_2=H$, $R_3=CH_3$, $X=NR_8$, $R_8=CN$)-FCE 22952

To a solution of 3.1 g (20 mmol) of 2-amino-4,5,6,7-tetrahydrothiazolo[5,4-c]pyridine in 40 ml of absolute ethanol, 4.09 (28 mmol) of N-cyano-S,S-dimethyl cyanodithioiminocarbonate (IV: $X''=NR_8$, $R_8=CN$) was added at room temperature. After standing for 30 hours, the reaction mixture was filtered to afford 2-amino-5-(methylthio-N-cyano-iminomethyl)-4,5,6,7-tetrahydrothiazolo[5,4-c]pyridine (V: $R_1=R_2=H$, n=0, $X''=R_8$, $R_8=CN$), m.p. 152°–155° C., in 85% yield. 4.33 g (17 mmol) of the compound V thus prepared was dissolved in 17 ml of absolute ethanol and treated at room temperature with a 33% solution of methylamine in 55 ml of ethanol. After 15 minutes the precipitate was filtered and crystallized from a 1:1 by volume mixture of acetonitrile:ethanol. 3.7 g (92% yield) of the title compound (m.p. 231°–234° C.) were obtained.

EXAMPLE 10

2-Amino-5-(N-cyano-N'-isopropyl-amidino)-4,5,6,7-tetrahydrothiazolo[5,4-c]pyridine (n=0, $R_1=R_2=H$, $R_3=CH(CH_3)_2$, $X=NR_8$, $R_8=CN$)-FCE 23098

Operating as in Example 9, but employing isopropylamine in place of methylamine, the title compound (m.p. 203°–205° C.) was obtained in 75% yield.

EXAMPLE 11

2-Amino-5-(N-cyano-N'-benzyl-amidino)-4,5,6,7-tetrahydrothiazolo[5,4-c]pyridine (n=0, $R_1=R_2=H$, $R_3=C_6H_5CH_2$, $X=NR_8$, $R_8=CN$)-FCE 23065

Operating as in Example 9, but employing benzylamine in place of methylamine, the title compound (m.p. 182°–183° C.) was obtained in 64% yield.

EXAMPLE 12

2-Amino-5-(N'-benzoyl-amidino)-4,5,6,7-tetrahydrothiazolo[5,4-c]pyridine (n=0, $R_1=R_2=H$, $R_3=COR_4$, $X=NR_8$, $R_8=H$, $R_4=C_6H_5$)-FCE 23181

2.33 g (15 mmol) of 2-amino-4,5,6,7-tetrahydrothiazolo[5,4-c]pyridine was dissolved in 30 ml of dimethylformamide and 2.63 g (18 mmol) of benzoylcyanamide was added. The reaction mixture was kept at 70° C. for an hour and at 110° C. for a further hour. The solvent was removed by evaporation and the residue (about 5 g) was crystallized from acetonitrile. 3.5 g (78% yield) of the pure title compound (m.p. 180°–181° C.) with decomposition) were obtained.

EXAMPLE 13

2-Amino-5-(N'-methyl-N-tosyl-amidino)-4,5,6,7-tetrahydrothiazolo[5,4-c]pyridine (n=0, $R_1=R_2=H$, $R_3=CH_3$, $X=NR_8$, $R_8=SO_2C_6H_4CH_3$)-FCE 23477

To a solution of 8.26 g (30 mmol) of N-tosyl-S,S-dimethyl dithioimino carbonate (IV: $X''=NR_8$, $R_8=p.CH_3.C_6H_4.SO_2$) in 80 ml of absolute ethanol, 3.88 g (25 mmol) of 2-amino-4,5,6,7-tetrahydrothiazolo[5,4-c]pyridine was added. The reaction mixture was refluxed for 28 hours. The ethanol was then removed by evaporation in vacuo and the crude residue was chromatographed on a silica gel column using ethyl acetate with increasing methanol as eluant. 6.05 g (63% yield) of 2-amino-5-(methylthio-N-tosyliminomethyl)-4,5,6,7-tetrahydrothiazolo[5,4-c]pyridine (V: $R_1=R_2=H$, n=0, $X''=NR_8$, $R_8=p.CH_3.C_6H_4SO_2$) m.p. 191°–195° C., were obtained. This compound was dissolved in 110 ml of absolute ethanol and treated with a 33% solution of methylamine in 5.88 ml of ethanol. The reaction mixture was refluxed for about 5 hours. The solvent was then removed by evaporation in vacuo and the residue (about 6 g) was crystallized from acetonitrile. 4.38 g (76% yield) of the pure title compound (m.p. 206°–208° C.) were obtained.

EXAMPLE 14

2-Amino-5-(N'-methyl-N-benzoyl-amidino)-4,5,6,7-tetrahydrothiazolo[5,4-c]pyridine (n=0, $R_1=R_2=H$, $R_3=CH_3$, $X=NR_8$, $R=COC_6H_5$)-FCE 23495

To a solution of 5.4 g (24 mmol) of N-benzoyl-S,S-dimethyl dithioiminocarbonate (IV: $X''=NR_8$, $R_8=C_6H_5CO$) in 50 ml of absolute ethanol, 3.1 g (20 mmol) of 2-amino-4,5,6,7-tetrahydrothiazolo[5,4-c]pyridine was added at room temperature. After standing for 31 hours, the reaction mixture was evaporated to dryness in vacuo. The residue (V: $R_1=R_2=H$, n=0, $X'=NR_8$, $R_8=C_6H_5CO$: about 8.5 g) was dissolved in 50 ml of absolute ethanol and treated at room temperature with a 33% solution of methylamine in 10 ml of ethanol. After about 8 hours the solvent was removed by evaporation and the residue (about 7.5 g) was crystallized from acetonitrile. 5.6 g (88% yield) of the pure title compound (m.p. 124°–128° C.) were obtained.

EXAMPLE 15

2-Guanidino-5-(isopropyl-thiocarbamoyl)-4,5,6,7-tetrahydrothiazolo[5,4-c]pyridine (n=0, $R_1 = H_2NC=NH,$
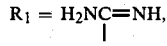

$R_2=H$, $R_3=CH(CH_3)_2$, X=S)-FCE 22940

To a solution of 0.986 g (5 mmol) of 2-guanidino-4,5,6,7-tetrahydrothiazolo[5,4-c]pyridine in 15 ml of dimethylformamide, 0.606 g (6 mmol) of isopropyl isothiocyanate was added after cooling at 0° C. After 7 hours, the solvent was removed by evaporation and the residue (about 1.6 g) was crystallized from acetonitrile.

1.24 g (83% yield) of the pure title compound (m.p. 238° C. with decomposition) were obtained.

EXAMPLE 16

2-Guanidino-5-(isopropyl-carbamoyl)-4,5,6,7-tetrahydrothiazolo[5,4-c]pyridine (n=0,

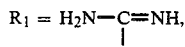

$R_2=H$, $R_3=CH(CH_3)_2$, $X=O$)-FCE 23067

Operating as in Example 15, but employing isopropyl isocyanate in place of isopropyl isothiocyanate, the title compound (m.p. 210°–213° C. with decomposition) was obtained in 70% yield.

EXAMPLE 17

2-Guanidino-5-(N'-methyl-N-cyano-amidino)-4,5,6,7-tetrahydrothiazolo[5,4-c]pyridine (n=0,

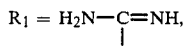

$R_2=H$, $R_3=CH_3$, $X=NR_8$, $R_8=CN$)-FCE 23171

To a suspension of 3.95 g (20 mmol) of 2-guanidino-4,5,6,7-tetrahydrothiazolo[5,4-c]pyridine in 40 ml of absolute ethanol, 3.51 g (24 mmol) of N-cyano-S,S-dimethyldithioimidocarbonate (IV: $X''=NR_8$, $R_8=CN$) was added at room temperature. After standing for 30 hours, the reaction mixture was evaporated to dryness and the crude residue was chromatographed on a silica gel column using ethyl acetate with increasing methanol as eluant. 4.7 g (80% yield) of 2-guanidino-5-(methylthio-N-cyano-imino-methyl)-4,5,6,7-tetrahydrothiazolo[5,4-c]pyridine (V:

$R_2=R_6=R_7=H$, $n=0$, $X''=NR_8$, $R_8=CN$), m.p. 224°–227° C., were obtained. This compound was treated with a 33% solution of methylamine in 93 ml of ethanol at room temperature. After standing for 24 hours the solid compound was filtered and crystallized from methanol. 2.21 g (50% yield) of the title compund (m.p. 243°–246° C. with decomposition) were obtained.

EXAMPLE 18

2-Guanidino-5-(N'-benzoyl-amidino)-4,5,6,7-tetrahydrothiazolo[5,4-c]pyridine (n=0,

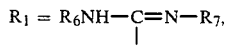

$R_2=H$, $R_3=COR_4$, $X=NR_8$, $R_8=H$, $R_4=C_6H_5$)-FCE 23184

To a solution of 2.96 g (15 mmol) of 2-guanidino-4,5,6,7-tetrahydrothiazolo[5,4-c]pyridine in 30 ml of dimethylformamide, 2.74 g (18.75 mmol) of benzoyl-cyanamide was added. The reaction mixture was kept at 110° C. for 2 hours, and then the solvent was removed by evaporation. The residue (about 6 g) was crystallized from acetonitrile. 2.06 g (40% yield) of the pure title compound (m.p. 243°–246° C.) were obtained.

EXAMPLE 19

2-Guanidino-5-(N'-methyl-N-tosyl-amidino)-4,5,6,7-tetrahydrothiazolo[5,4,-c]pyridine (n=0,

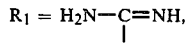

$R_2=H$, $R_3=CH_3$, $X=NR_8$, $R_8=SO_2C_6H_4CH_3$)-FCE 23494

2.96 g (15 mmol) of 2-guanidino-4,5,6,7-tetrahydrothiazolo[5,4,-c]pyridine was added at room temperature to a suspension of 6.2 g (22.5 mmol) of N-tosyl-S,S-dimethyl dithioiminocarbonate (IV: $X''=NR_8$, $R_8=p.CH_3.C_6H_4SO_2$) in 45 ml of absolute ethanol. After standing for 16 hours, the reaction mixture was refluxed for about 13 hours and was then evaporated to dryness in vacuo. The crude residue, about 6 g of 2-guanidino-5-(methylthio-N-tosyl-iminomethyl)-4,5,6,7-tetrahydrothiazolo[5,4,-c]pyridine (V: $R_1=H$;

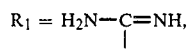

$R_6=R_7=H$; $n=0$; $X''=NR_8$; $R_8=p.CH_3.C_6H_4SO_2$), was dissolved in 105 ml of absolute ethanol and treated with a 33% solution of methylamine in 9.3 ml of ethanol. The reaction mixture was refluxed for 7 hours, and then evaporated to dryness in vacuo. The residue (about 6 g) was crystallized from acetonitrile. 2.87 g (47% yield) of the pure title compound (m.p. 229°–232° C. with decomposition) were obtained.

EXAMPLE 20

2-Guanidino-5-(N'-methyl-N-benzoyl-amidino)-4,5,6,7-tetrahydrothiazolo[5,4,-c]pyridine (n=0,

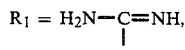

$R_2=H$, $R_3=CH_3$, $X=NR_8$, $R_8=COC_6H_5$)-FCE 23496

2.96 g (15 mmol) of 2-guanidino-4,5,6,7-tetrahydrothiazolo[5,4,-c]pyridine was added at room temperature to a solution of 4.06 g (18 mmol) of N-benzoyl-S,S-dimethyl dithiominocarbonate (IV: $X''=NR_8$, $R_8=C_6H_5CO$) in 75 ml of absolute ethanol. After standing for 24 hours, the reaction mixture was filtered to afford 2-guanidino-5-(methylthio-N-benzoyliminomethyl)-4,5,6,7-tetrahydrothiazolo[5,4,-c]pyridine (V:

$R_1 = R_6-NH-C=N-R_7$, $n=0$, $X''=NR_8$, 70% yield.

4 g (10.68 mmol) of this compound was dissolved in 90 ml of absolute ethanol and treated at room temperature with a 33% solution of methylamine in 9.31 ml of ethanol. After about 11 hours the product was filtered

EXAMPLE 21

2-(N,N'-dicyclohexylguanidino)-5-isopropylcarbamoyl-4,5,6,7-tetrahydrothiazolo[5,4,-c]pyridine. (n=0,

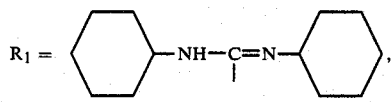

R$_2$=H, R$_3$=isoC$_3$H$_7$, X=0)

To a solution of 2.4 g (10 mmol) of 2-amino-5-isopropyl-carbamoyl-4,5,6,7-tetrahydrothiazolo[5,4,-c]pyridine in 20 ml of anhydrous dimethylformamide, 0.337 g (3 mmol) of pyridine hydrochloride and 3.09 g (15 mmol) of N,N'-dicyclohexylcarbodiimide dissolved in 5 ml of anhydrous dimethylformamide was added at room temperature under a nitrogen atmosphere. After standing for 4 days, the solvent was removed by evaporation in vacuo and the residue was dissolved in iced water. The aqueous solution was made strongly alkaline with 2N sodium hydroxide and extracted with methylene chloride. The extracts were dried over anhydrous sodium sulfate and evaporated to dryness. The residue (about 5 g) was chromatographed on a silica gel column using ethyl acetate as eluant. 2.2 g (50% yield) of the pure title compound was obtained as a white foam.

$^1$H-NMR or the title compound (CDCl$_3$, 200 MHz):

1.15 δ (d, 6H, CH(C$\underline{H}$$_3$)$_2$)

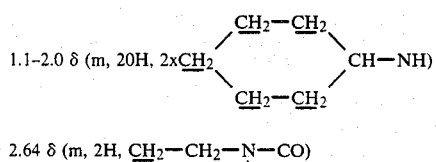

2.64 δ (m, 2H, C$\underline{H}$$_2$—CH$_2$—N—CO)

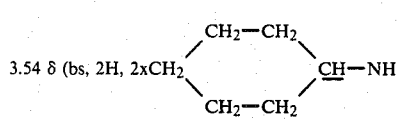

3.67 δ (t, 2H, CH$_2$—C$\underline{H}$$_2$—N—CO)

4.00 δ (m, 1H, NH—C$\underline{H}$(CH$_3$)$_2$)

4.26 δ (d, 1H, N$\underline{H}$—CH(CH$_3$)$_2$)

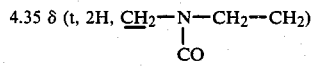

EXAMPLE 22

2-Guanidino-5-(cyclopropyl-carbamoyl)-4,5,6,7-tetrahydrothiazolo[5,4,-c]pyridine (n=0

R$_1$ = H$_2$N—C=NH;

R$_2$=H; R$_3$=cyclopropyl; X×0)-FCE 23712

Operating as in Example 15, but employing cyclopropyl isocyanate in place of isopropyl isothiocyanate, the title compound (m.p. 215°–216° C. with decomposition) was obtained in 50% yield.

EXAMPLE 23

2-Guanidino-5-(cyclopentyl-carbamoyl)-4,5,6,7-tetrahydrothiazolo[5,4,-c]pyridine (n=0;

R$_1$ = H$_2$N—C=NH;

R$_2$=H; R$_3$=cyclopentyl; X=0)-FCE 23849

Operating as in Example 15, but employing cyclopentyl isocyanate in place of isopropyl isothiocyanate, the title compound (m.p. 228°–229° C. with decomposition) was obtained in 60% yield.

EXAMPLE 24

2-Guanidino-5-(methyl-carbamoyl)-4,5,6,7-tetrahydrothiazolo[5,4,-c]pyridine (n=0;

R$_1$ = H$_2$N—C=NH;

R$_2$=H; R$_3$=Me; X=0)-FCE 23902

Operating as in Example 15, but employing methyl isocyanate in place of isopropyl isothiocyanate, the title compound (m.p. 236° C. with decomposition) was obtained in 62% yield.

EXAMPLE 25

2-Guanidino-5-(cyclohexyl-carbamoyl)-4,5,6,7-tetrahydrothiazolo[5,4,-c]pyridine (n=0;

R$_1$ = H$_2$N—C=NH;

R$_2$=H; R$_3$=cyclohexyl; X=0)-FCE 23942

Operating as in Example 15, but employing cyclohexyl isocyanate in place of isopropyl isothiocyanate, the title compound (m.p. 225° C. with decomposition) was obtained in 49% yield.

EXAMPLE 26

2-Guanidino-5-(tosyl-carbamoyl)-4,5,6,7-tetrahydrothiazolo[5,4,-c]pyridine (n=0;

R$_1$ = H$_2$N—C=NH;

R$_2$=H; R$_3$=tosyl; X=0)-FCE 24004

Operating as in Example 15, but employing tosyl isocyanate in place of isopropyl isothiocyanate, the title compound (m.p. 227°–228° C.) was obtained in 16% yield.

EXAMPLE 27

2-Guanidino-5-(ethyl-carbamoyl)-4,5,6,7-tetrahydro-thiazolo[5,4,-c]pyridine (n=0;

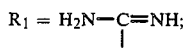

R$_2$=H; R$_3$=ethyl; X=O)-FCE 23959

Operating as in Example 15, but employing ethyl isocyanate in place of isopropyl isothiocyanate, the title compound (m.p. 224°–245° C. with decomposition) was obtained in 53% yield.

EXAMPLE 28

2-Guanidino-5-(n-propyl-carbamoyl)-4,5,6,7-tetrahydrothiazolo[5,4,-c]pyridine (n=0;

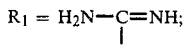

R$_2$=H; R$_3$=n-propyl; X=O)-FCE 24011

Operating as in Example 15, but employing n-propyl isocyanate in place of isopropyl isothiocyanate, the title compound (m.p. 201°–202° C. with decomposition) was obtained in 64% yield.

EXAMPLE 29

2-Guanidino-5-(n-butyl-carbamoyl)-4,5,6,7-tetrahydrothiazolo[5,4,-c]pyridine (n=0;

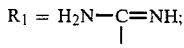

R$_2$=H; R$_3$=n-butyl; X=O)-FCE 24028

Operating as in Example 15, but employing n-butyl isocyanate in place of isopropyl isothiocyanate, the title compound (m.p. 220° C.) was obtained in 50% yield.

EXAMPLE 30

2-(N,N-dimethylaminomethyl)-5-(N-isopropylthiocarbamoyl)-4,5,6,7-tetrahydrothiazolo[5,4,-c]pyridine
(n=1, R$_1$=R$_2$=CH$_3$, R$_3$=i-propyl, X=S)-FCE 23733

To a solution of 2-(N,N-dimethylaminomethyl)-4,5,6,7-tetrahydrothiazolo[5,4,-c]pyridine (1.97 g, 10 mmol) in acetonitrile (15 ml), isopropylisothiocyanate (1.01 g, 10 mmol) was added at room temperature and the reaction mixture was refluxed for 30 minutes. The solvent was evaporated to dryness and the residue (about 3 g) crystallized from diisopropyl ether. 1.91 g (64% yield) of the pure title compound (m.p. 123° C.) were obtained.

EXAMPLE 31

2-(N,N-dimethylaminomethyl)-5-(N-isopropylcarbamoyl)-4,5,6,7-tetrahydrothiazolo[5,4,-c]pyridine.
(n=1, R$_1$=R$_2$=CH$_3$, R$_3$=i-propyl, X=O)-FCE 23779

Operating as in Example 30 but employing isopropylisocyanate, the title compound (m.p. 150° C.) was obtained in 46% yield.

EXAMPLE 32

2-(N,N-dimethylaminomethyl)-5-(N-cyano-N'-methyl-quanyl)-4,5,6,7-tetrahydrothiazolo[5,4,-c]pyridine
(n=1, R$_1$=R$_2$=R$_3$=CH$_3$, X=N-CN)-FCE 23787

To a solution of 2-(N,N-dimethylaminomethyl)-4,5,6,7-tetrahydrothiazolo[5,4,-c]pyridine (1.97 g, 10 mmol) in absolute ethanol (15 ml), dimethyl cyanodithioimidocarbonate (IV: X''=NR$_8$; R$_8$=CN; 1.46 g, 10 mmol) was added at room temperature. After standing for 3 hours, the reaction mixture was heated at 65° C. over a period of one hour and a half. The solvent was evaporated in vacuo and the residue, mainly constituted by the crude (V) (R$_1$=R$_2$=CH$_3$; n=1, X'=NR$_8$; R$_8$=CN; about 2.9 g) was dissolved in absolute ethanol (10 ml) and treated at room temperature with a 33% solution of methylamine in ethanol (2.5 ml). After standing for 2 hours, the reaction mixture was heated at 70° C. for 30 minutes. The solvent was evaporated in vacuo and the residue (about 2.7 g) crystallized from acetonitrile. 1.44 g (50% yield) of the pure title compound (m.p. 160° C.) were obtained.

Operating as described in the previous examples, the following compounds were also prepared:

2-quanidino-5-(phenyl-carbamoyl)-4,5,6,7-tetrahydrothiazolo[5,4,-c]pyridine, 2-quanidino-5-(phenyl-thiocarbamoyl)-4,5,6,7-tetrahydrothiazolo[5,4,-c]pyridine, 2-guanidino-5-(benzyl-carbamoyl)-4,5,6,7-tetrahydrothiazolo[5,4, -c]pyridine, 2-amino-5-(4'-chlorophenyl-carbamoyl)-4,5,6,7-tetrahydrothiazolo[5,4,-c]pyridine, 2-guanidino-5-(4'-chlorophenyl-carbamoyl)-4,5,6,7-tetrahydrothiazolo[5,4,-c]pyridine, 2-amino-5-(2'-phenylethyl-carbamoyl)-4,5,6,7-tetrahydrothiazolo[5,4,-c]pyridine, 2-quanidino-5-(2'-phenylethyl-carbamoyl)-4,5,6,7-tetrahydrothiazolo[5,4,-c]pyridine, 2-amino-5-(cyclobutyl-carbamoyl)-4,5,6,7-tetrahydrothiazolo[5,4,-c]pyridine, 2-guanidino-5-(cyclobutyl-carbamoyl)-4,5,6,7-tetrahydrothiazolo[5,4,-c]pyridine.

Having now fully described the invention, it will be apparent to one of ordinary skill in the art that many changes and modifications can be made thereto without departing from the spirit and scope of the invention as set forth herein:

What is claimed as new and desired to be secured by Letters Patent of the United States is:

1. A compound of formula I:

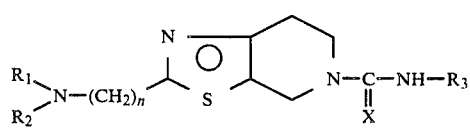

wherein n is zero or 1;
either (i) each of R$_1$ and R$_2$ independently is a hydrogen atom or an alkyl group of from 1 to 6 carbon atoms, or
(ii) R$_2$ is a hydrogen atom and R$_1$ is an amidino group of the formula;

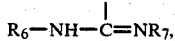

wherein each of $R_6$ and $R_7$ independently is a hydrogen atom or a $C_3$–$C_7$ cycloalkyl group;

X is an oxygen or sulfur atom, or is an imino, cyanoimino, p-toluenesulfonylimino group or a benzoylimino group; and $R_3$ is $C_1$–$C_6$ alkyl, $C_3$–$C_7$ cycloalkyl, phenyl, phenylethyl, chlorophenyl, benzyl, benzoyl or p-toluenesulfonyl; or a pharmaceutically acceptable acid addition salt thereof.

2. The compound of claim 1, which is 2-guanidino-5-(isopropyl-carbamoyl)-4,5,6,7-tetrahydrothiazolo[5,4,-c]pyridine, or a pharmaceutically acceptable salt thereof.

3. The compound of claim 1, which is selected from the group consisting of:
2-amino-5-(methyl-thiocarbamoyl)-4,5,6,7-tetrahydrothiazolo[5,4,-c]pyridine,
2-amino-5-(isopropyl-thiocarbamoyl)-4,5,6,7-tetrahydrothiazolo[5,4,-c]pyridine,
2-amino-5-(phenyl-thiocarbamoyl)-4,5,6,7-tetrahydrothiazolo[5,4,-c]pyridine,
2-amino-5-(benzoyl-thiocarbamoyl)-4,5,6,7-tetrahydrothiazolo[5,4,-c]pyridine,
2-amino-5-(methyl-carbamoyl)-4,5,6,7-tetrahydrothiazolo[5,4,-c]pyridine,
2-amino-5-(isopropyl-carbamoyl)-4,5,6,7-tetrahydrothiazolo[5,4,-c]pyridine,
2-amino-5-(phenyl-carbamoyl)-4,5,6,7-tetrahydrothiazolo[5,4,-c]pyridine,
2-amino-5-(N-benzylcarbamoyl)-4,5,6,7-tetrahydrothiazolo[5,4,-c]pyridine,
2-amino-5-(N-cyano-N'-methyl-amidino)-4,5,6,7-tetrahydrothiazolo[5,4,-c]pyridine,
2-amino-5-(N-cyano-N'-isopropyl-amidino)-4,5,6,7-tetrahydrothiazolo[5,4,-c]pyridine,
2-amino-5-(N-cyano-N'-benzyl-amidino)-4,5,6,7-tetrahydrothiazolo[5,4,-c]pyridine,
2-amino-5-(N'-benzoyl-amidino)-4,5,6,7-tetrahydrothiazolo[5,4,-c]pyridine,
2-amino-5-(N'-methyl-N-tosyl-amidino)-4,5,6,7-tetrahydrothiazolo[5,4,-c]pyridine,
2-amino-5-(N'-methyl-N-benzoyl-amidino)-4,5,6,7-tetrahydrothiazolo[5,4,-c]pyridine,
2-guanidino-5-(isopropyl-thiocarbamoyl)-4,5,6,7-tetrahydrothiazolo[5,4,-c]pyridine,
2-guanidino-5-(N'-methyl-N-cyano-amidino)-4,5,6,7-tetrahydrothiazolo[5,4,-c]pyridine,
2-guanidino-5-(N'-benzoyl-amidino)-4,5,6,7-tetrahydrothiazolo[5,4,-c]pyridine,
2-guanidino-5-(N'-methyl-N-tosyl-amidino)-4,5,6,7-tetrahydrothiazolo[5,4,-c]pyridine,
2-guanidino-5-(N'-methyl-N-benzoyl-amidino)-4,5,6,7-tetrahydrothiazolo[5,4,-c]pyridine,
2-(N,N'-dicyclohexylguanidino)-5-isopropylcarbamoyl-4,5,6,7-tetrahydrothiazolo[5,4,-c]pyridine,
2-guanidino-5-(cyclopropyl-carbamoyl)-4,5,6,7-tetrahydrothiazolo[5,4,-c]pyridine,
2-guanidino-5-(cyclopentyl-carbamoyl)-4,5,6,7-tetrahydrothiazolo[5,4,-c]pyridine,
2-guanidino-5-(methyl-carbamoyl)-4,5,6,7-tetrahydrothiazolo[5,4,-c]pyridine,
2-guanidino-5-(cyclohexyl-carbamoyl)-4,5,6,7-tetrahydrothiazolo[5,4,-c]pyridine,
2-guanidino-5-(tosyl-carbamoyl)-4,5,6,7-tetrahydrothiazolo[5,4,-c]pyridine,
2-guanidino-5-(ethyl-carbamoyl)-4,5,6,7-tetrahydrothiazolo[5,4,-c]pyridine,
2-guanidino-5-(n-propyl-carbamoyl)-4,5,6,7-tetrahydrothiazolo[5,4,-c]pyridine,
2-guanidino-5-(n-butyl-carbamoyl)-4,5,6,7-tetrahydrothiazolo[5,4,-c]pyridine,
2-(N,N-dimethylaminomethyl)-5-(N-isopropylthiocarbamoyl)-4,5,6,7-tetrahydrothiazolo[5,4,-c]pyridine,
2-(N,N-dimethylaminomethyl)-5-(N-isopropylcarbamoyl)-4,5,6,7-tetrahydrothiazolo[5,4,-c]pyridine,
2-(N,N-dimethylaminomethyl)-5-(N-cyano-N'-methyl-guanyl)-4,5,6,7-tetrahydrothiazolo[5,4,-c]pyridine,
2-amino-5-((2'-phenylethyl-carbamoyl)-4,5,6,7-tetrahydrothiazolo[5,4,-c]pyridine,
2-guanidino-5-(2'-phenylethyl-carbamoyl)-4,5,6,7-tetrahydrothiazolo[5,4,-c]pyridine,
2-guanidino-5-(phenyl-carbamoyl)-4,5,6,7-tetrahydrothiazolo[5,4,-c]pyridine,
2-guanidino-5-(phenyl-thiocarbamoyl)-4,5,6,7-tetrahydrothiazolo[5,4,-c]pyridine,
2-guanidino-5-(benzyl-carbamoyl)-4,5,6,7-tetrahydrothiazolo[5,4,-c]pyridine,
2-amino-5-(4'-chlorophenyl-carbamoyl)-4,5,6,7-tetrahydrothiazolo[5,4,-c]pyridine,
2-guanidino-5-(5'-chlorophenyl-carbamoyl)-4,5,6,7-tetrahydrothiazolo[5,4,-c]pyridine,
2-amino-5-(cyclobutyl-carbamoyl)-4,5,6,7-tetrahydrothiazolo[5,4,-c]pyridine, and
2-guanidino-5-(cyclobutyl-carbamoyl)-4,5,6,7-tetrahydrothiazolo[5,4,-c]pyridine.

4. A pharmaceutical composition having anti-ulcerogenic and anti-secretory activity, comprising:
a therapeutically effective amount of the compound of claim 1, in admixture with a pharmaceutically acceptable diluent or carrier.

5. A pharmaceutical composition having anti-ulcerogenic and anti-secretory activity, comprising:
a therapeutically effective amount of the compound of claim 2, in admixture with a pharmaceutically acceptable diluent or carrier.

6. A pharmaceutical composition having anti-ulcerogenic and anti-secretory activity, comprising:
a therapeutically effective amount of the compound of claim 3, in admixture with a pharmaceutically acceptable diluent or carrier.

7. A method for treating peptic ulcers in humans, which method comprises:
administering to a subject in need of such treatment a therapeutically effective amount of the compound of claim 1.

8. A method for treating peptic ulcers in humans, which method comprises:
administering to a subject in need of such treatment a therapeutically effective amount of the pharmaceutical composition of claim 4.

9. A method for treating peptic ulcers in humans, which method comprises:
administering to a subject in need of such treatment a therapeutically effective amount of the pharmaceutical composition of claim 5.

10. A method for treating peptic ulcers in humans, which method comprises:
administering to a subject in need of such treatment a therapeutically effective amount of the pharmaceutical composition of claim 6.

* * * * *

UNITED STATES PATENT AND TRADEMARK OFFICE
CERTIFICATE OF CORRECTION

PATENT NO. : 4,624,956
DATED : November 25, 1986
INVENTOR(S) : LAZZARINI ET AL

It is certified that error appears in the above-identified patent and that said Letters Patent is hereby corrected as shown below:

Column 7, line 60, change "X=3)-FCE 2282" to --X=S)-FCE 22882--.

Column 8, line 40, change "isocyanate" to --isothiocyanate--;

line 47, change "2306" to --23026--;

line 55, change "$R_1$=H" to --$R_1=R_2$=H--.

Column 14, line 1, change "X ✗ O" to --X=O--.

Signed and Sealed this

Twenty-second Day of March, 1988

Attest:

DONALD J. QUIGG

*Attesting Officer*  *Commissioner of Patents and Trademarks*